United States Patent
Itu et al.

(10) Patent No.: US 10,779,785 B2
(45) Date of Patent: Sep. 22, 2020

(54) SEMANTIC SEGMENTATION FOR CANCER DETECTION IN DIGITAL BREAST TOMOSYNTHESIS

(71) Applicant: Siemens Healthcare GmbH, Erlangen (DE)

(72) Inventors: Lucian Mihai Itu, Brasov (RO); Laszlo Lazar, Gheorgheni (RO); Siqi Liu, Princeton, NJ (US); Olivier Pauly, Munich (DE); Philipp Seegerer, Fuerstenzell (DE); Iulian Ionut Stroia, Brasov (RO); Alexandru Turcea, Busteni (RO); Anamaria Vizitiu, Sfantu Gheorghe (RO); Daguang Xu, Princeton, NJ (US); Shaohua Kevin Zhou, Plainsboro, NJ (US)

(73) Assignee: SIEMENS HEALTHCARE GMBH, Erlangen (DE)

( * ) Notice: Subject to any disclaimer, the term of this patent is extended or adjusted under 35 U.S.C. 154(b) by 207 days.

(21) Appl. No.: 16/033,332

(22) Filed: Jul. 12, 2018

(65) Prior Publication Data

US 2019/0015059 A1    Jan. 17, 2019

(30) Foreign Application Priority Data

Jul. 17, 2017 (EP) .................................. 17464009

(51) Int. Cl.
*G06K 9/00* (2006.01)
*A61B 6/00* (2006.01)
(Continued)

(52) U.S. Cl.
CPC .............. *A61B 6/502* (2013.01); *A61B 6/025* (2013.01); *A61B 6/032* (2013.01); *A61B 6/5205* (2013.01);
(Continued)

(58) Field of Classification Search
CPC ......... A61B 6/025; A61B 6/032; A61B 6/502; A61B 6/5205; G06F 17/175;
(Continued)

(56) References Cited

U.S. PATENT DOCUMENTS

2017/0046616 A1* 2/2017 Socher ................... G06N 3/088
2017/0200067 A1   7/2017 Zhou et al.
(Continued)

OTHER PUBLICATIONS

Samala Ravi K et al: "Deep-learning convolution neural network for computer-aided detection of microcalcifications in digital breast tomosynthesis", Progress in Biomedical Optics and Imaging, SPIE—International Society for Optical Engineering, Bellingham, WA, US, vol. 9785, Mar. 24, 2016 (Mar. 24, 2016), pp. 97850Y-97850Y; XP060070471; ISSN: 1605-7422, DOI: 10.1117/12.2217092 ISBN: 978-1-5106-0027-0; 2016.
(Continued)

*Primary Examiner* — Tom Y Lu
(74) *Attorney, Agent, or Firm* — Harness, Dickey & Pierce, P.L.C.

(57) ABSTRACT

A method, apparatus and non-transitory computer readable medium are for segmenting different types of structures, including cancerous lesions and regular structures like vessels and skin, in a digital breast tomosynthesis (DBT) volume. In an embodiment, the method includes: pre-classification of the DBT volume in dense and fatty tissue and based on the result; localizing a set of structures in the DBT volume by using a multi-stream deep convolutional neural network; and segmenting the localized structures by calculating a probability for belonging to a specific type of structure for each voxel in the DBT volume by using a deep convolutional neural network for providing a three-dimensional probabilistic map.

23 Claims, 4 Drawing Sheets

(51) Int. Cl.

| | |
|---|---|
| *A61B 6/02* | (2006.01) |
| *A61B 6/03* | (2006.01) |
| *G06T 7/00* | (2017.01) |
| *G06T 11/00* | (2006.01) |
| *G06T 7/143* | (2017.01) |
| *G06K 9/46* | (2006.01) |
| *G06F 17/17* | (2006.01) |
| *G06F 16/28* | (2019.01) |
| *G06T 7/11* | (2017.01) |

(52) U.S. Cl.
CPC .......... *G06F 16/285* (2019.01); *G06F 17/175* (2013.01); *G06K 9/46* (2013.01); *G06T 7/0012* (2013.01); *G06T 7/11* (2017.01); *G06T 7/143* (2017.01); *G06T 11/006* (2013.01); *G06T 2200/04* (2013.01); *G06T 2207/10112* (2013.01); *G06T 2207/20012* (2013.01); *G06T 2207/20016* (2013.01); *G06T 2207/20076* (2013.01); *G06T 2207/20081* (2013.01); *G06T 2207/20084* (2013.01); *G06T 2207/30068* (2013.01); *G06T 2211/40* (2013.01)

(58) Field of Classification Search
CPC ... G06F 16/285; G06F 17/30598; G06K 9/46; G06T 11/006; G06T 2207/10112; G06T 2207/30068; G06T 2211/40; G06T 7/0012; G06T 7/143; G06T 2200/04; G06T 2207/20012; G06T 2207/20016; G06T 2207/20076; G06T 2207/20081; G06T 2207/20084; G06T 7/11
See application file for complete search history.

(56) References Cited

U.S. PATENT DOCUMENTS

| | | | |
|---|---|---|---|
| 2018/0033144 A1* | 2/2018 | Risman | G06T 7/0012 |
| 2018/0075628 A1* | 3/2018 | Teare | A61B 6/461 |

OTHER PUBLICATIONS

Dhungel, Neeraj et al.: "A Deep Learning Approach for the Analysis of Mases in Mammograms with Minimal User Intervention", in: Journal of Medical Image Analysis, Jan. 26, 2017, pp. 1-43.

Litjens, Geert et al.: "A Survey on Deep Learning in Medical Image Analysis", in: Diagnostic Image Analysis Group, 2017, pp. 1-34; arxiv.org, Cornell University Library, 201Olin Library Cornell University Ithaca; NY 14853; XP080747655.

Samala Ravi K et al: "Mass detection in digital breast tomosynthesis: Deep convolutional neural network with transfer learning from mammography", Medical Physics, AIP, Melville, NY, US, vol. 43, No. 12, Nov. 29, 2016 (Nov. 29, 2016), pp. 6654-6666, XP012214029, ISSN: 0094-2405, DOI: 10.1118/1.4967345; 2016.

Fotin Sergei V et al: "Detection of soft tissue densities from digital breast tomosynthesis: comparison of conventional and deep learning approaches", Progress in Biomedical Optics and Imaging, SPIE—International Society for Optical Engineering, Bellingham, WA, US, vol. 9785, Mar. 24, 2016 (Mar. 24, 2016), pp. 97850X-97850X, XP060070470, ISSN: 1605-7422, DOI: 10.1117/12.2217045 ISBN: 978-1-5106-0027-0; 2016.

Ciompi Francesco et al: "Towards automatic pulmonary nodule management in lung cancer screening with deep learning"; Obesity, Fitness & Wellness Week, May 6, 2017 (May 6, 2017), p. 429; XP055431761; Retrieved from the Internet: URL:https://arxiv.org/pdf/1610.09157.pdf; 2017.

* cited by examiner

SEMANTIC SEGMENTATION FOR CANCER DETECTION IN DIGITAL BREAST TOMOSYNTHESIS

PRIORITY STATEMENT

The present application hereby claims priority under 35 U.S.C. § 119 to European patent application number EP17464009.4 filed Jul. 17, 2017, the entire contents of which are hereby incorporated herein by reference.

FIELD

At least one embodiment of the present invention generally relates to a method, apparatus and product for processing three-dimensional digital breast tomosynthesis images for cancer diagnosis.

BACKGROUND

Conventional mammography techniques rely on a pair of two-dimensional X-ray images of the female breast, taken from two different directions with the breast being compressed in different ways. The breast tissue to be examined is compressed and held between two compression plates to ensure that the entire breast tissue is viewed. Nowadays, full-field digital mammography systems (FFDM) are commonly used. However, digital mammography is plagued by low sensitivity and high false-positive rates caused by low-contrast characteristics and image noise, while still having the problem of overlapping structures common to traditional projection radiographs. Reported false-negative rates on mammographic screening range from 8% to 66% and depend on a multitude of factors including, but not limited to, age, breast density, tumor sub-type, and misinterpretation of subtle malignant mammographic findings.

Due to these disadvantages of two-dimensional mammographic imaging, recently, digital breast tomosynthesis (DBT) is increasingly replacing common 2D mammography for differential diagnoses and is in discussion for screening. DBT images provide more information than regular FFDM images for early detection of anomalies and cancer. DBT provides 3D image volumes of the compressed breast that are reconstructed from multiple 2D projections acquired at varying angles. Being a 3D imaging modality DBT naturally allows superior spatial localization of suspicious lesions. A mediolateral-oblique (MLO) and, typically, a second craniocaudal (CC) scan is acquired during an examination. The breast is compressed differently for MLO and CC scans.

For reporting and surgical planning it is common clinical practice to mark the lesions in the scans and to communicate the rough localization of suspicious findings in the uncompressed breast via schematic 2D drawings. The latter naturally suffers from inaccuracies and can often only be dissolved by additional, potentially ionizing and costly, imaging. Providing more accurate lesion localization in the un-compressed breast, e.g., in terms of a 3D rendering view, without additional imaging has the potential not only to facilitate surgical planning and related procedures, e.g., placing pre-operative markers but also to resolve the problem of ambiguous mapping of multiple similarly looking lesions between CC, MLO DBT and FFDM scans including previously acquired images.

Recent advances in machine vision based on deep learning, e.g. deep neural networks or deep convolutional neural networks, and massive training sets such as ImageNet gathered a lot of attention and attracted a lot of investment. Indeed, they are reaching now so-called superhuman performances for tasks such as natural image classification. Such technology could also be applied to the medical image analysis field, for example for the detection and segmentation of organs and anatomical structures. While great improvements can be expected, the detection of pathologies such as lesions or tumors still remains challenging due to their heterogeneous appearance and shape, and the need of massive databases annotated by expert radiologists. The benefits of applying such systems in the context of screening could be however tremendous, as it would support radiologists in their increasing workload.

By providing 3D information on the breast anatomy, a DBT image reduces dramatically the amount of false positive findings arising from the superposition of normal fibroglandular tissues in conventional 2D mammography. On the other hand, DBT increases the workload of radiologist due to the larger amount of slices to be inspected.

In state of the art it is known to apply artificial neural networks (ANN) in the context of breast lesion detection and segmentation. In the respect it is referred to the paper "Dhungel, N., Carneiro, G., Bradley, A. P, A deep learning approach for the analysis of masses in mammograms with minimal user intervention. Medical Image Analysis (2017)". This paper proposes a semi-automatic 3 stages approach: 1) detection stage, 2) user feedback stage and 3) segmentation stage. In the detection stage, authors combine deep belief network and Gaussian mixture model as candidate generator followed by a false positive reduction approach based on convolutional neural network and Random forest. Subsequently, refinement is performed using Bayesian optimization.

In the second stage, lesion candidates are shown to the user who has to provide feedback by further rejecting false positives. In the third stage, segmentation is performed by using deep structured learning model followed by a level-set refinement approach. This approach does not refer to 3D DBT data but only to mammograms and necessitates user feedback of the training data set, which may demand high resources.

SUMMARY

At least one embodiment of the present invention improves and automates the processing of DBT images for cancer diagnosis and augments and extends the DBT image with processed semantic data for improved visualization.

To make diagnosis and lesion search more efficient, a solution, in at least one embodiment, is to provide an automated image analysis approach that would permit the radiologists to navigate efficiently through the data towards the most relevant locations.

Beneficial embodiments are subject to the claims the description and the figures.

According to a first embodiment, a method is disclosed for segmenting different types of breast structures, including pathologic structures, like cancerous lesions and calcifications and regular structures, like vessels, glandular structures, the nipple, the pectoralis muscle and skin, that are relevant for cancer diagnosis in a DBT volume. In at least one embodiment the method comprises:

Localizing a set of structures in the DBT volume by using at least one multi-stream deep image-to-image network, taking as input at least one image channel; and Segmenting the localized structures by calculating a probability for belonging to a specific type of structure for each voxel in the DBT volume by using at least one multi-stream deep image-to-image network, taking as input at least one image channel for providing a three-dimensional probabilistic map.

In another embodiment, the present invention refers to a computer program loadable into a memory of a digital computer comprising software code portions for executing the method according to one embodiment of the method above, when the computer program is run on the computer. The computer program may also be executed on a plurality of network nodes as a distributed system. The computer program may be stored on a non-transitory computer readable medium and/or may be downloaded form a server.

At least one embodiment of the invention relates also to a non-transitory machine-readable data carrier or a non-transitory computer readable medium on which the computer program described above is stored.

According to at least one example embodiment, the invention is directed to an apparatus for segmenting different types of structures, including cancerous lesions and regular structures like vessels and skin, in a DBT volume, comprising:

A localizer for localizing a set of structures in the DBT volume by using a multi-stream deep convolutional neural network;

A segmentation unit for segmenting the localized structures by calculating a probability for belonging to a specific type of structure for each voxel in the DBT volume by using a deep convolutional neural network for providing a three-dimensional probabilistic map.

BRIEF DESCRIPTION OF THE DRAWINGS

Embodiments of the invention are shown in the figures and explained in the following detailed description.

DETAILED DESCRIPTION OF THE EXAMPLE EMBODIMENTS

The drawings are to be regarded as being schematic representations and elements illustrated in the drawings are not necessarily shown to scale. Rather, the various elements are represented such that their function and general purpose become apparent to a person skilled in the art. Any connection or coupling between functional blocks, devices, components, or other physical or functional units shown in the drawings or described herein may also be implemented by an indirect connection or coupling. A coupling between components may also be established over a wireless connection. Functional blocks may be implemented in hardware, firmware, software, or a combination thereof.

Various example embodiments will now be described more fully with reference to the accompanying drawings in which only some example embodiments are shown. Specific structural and functional details disclosed herein are merely representative for purposes of describing example embodiments. Example embodiments, however, may be embodied in various different forms, and should not be construed as being limited to only the illustrated embodiments. Rather, the illustrated embodiments are provided as examples so that this disclosure will be thorough and complete, and will fully convey the concepts of this disclosure to those skilled in the art. Accordingly, known processes, elements, and techniques, may not be described with respect to some example embodiments. Unless otherwise noted, like reference characters denote like elements throughout the attached drawings and written description, and thus descriptions will not be repeated. The present invention, however, may be embodied in many alternate forms and should not be construed as limited to only the example embodiments set forth herein.

It will be understood that, although the terms first, second, etc. may be used herein to describe various elements, components, regions, layers, and/or sections, these elements, components, regions, layers, and/or sections, should not be limited by these terms. These terms are only used to distinguish one element from another. For example, a first element could be termed a second element, and, similarly, a second element could be termed a first element, without departing from the scope of example embodiments of the present invention. As used herein, the term "and/or," includes any and all combinations of one or more of the associated listed items. The phrase "at least one of" has the same meaning as "and/or".

Spatially relative terms, such as "beneath," "below," "lower," "under," "above," "upper," and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below," "beneath," or "under," other elements or features would then be oriented "above" the other elements or features. Thus, the example terms "below" and "under" may encompass both an orientation of above and below. The device may be otherwise oriented (rotated 90 degrees or at other orientations) and the spatially relative descriptors used herein interpreted accordingly. In addition, when an element is referred to as being "between" two elements, the element may be the only element between the two elements, or one or more other intervening elements may be present.

Spatial and functional relationships between elements (for example, between modules) are described using various terms, including "connected," "engaged," "interfaced," and "coupled." Unless explicitly described as being "direct," when a relationship between first and second elements is described in the above disclosure, that relationship encompasses a direct relationship where no other intervening elements are present between the first and second elements, and also an indirect relationship where one or more intervening elements are present (either spatially or functionally) between the first and second elements. In contrast, when an element is referred to as being "directly" connected, engaged, interfaced, or coupled to another element, there are no intervening elements present. Other words used to describe the relationship between elements should be interpreted in a like fashion (e.g., "between," versus "directly between," "adjacent," versus "directly adjacent," etc.).

The terminology used herein is for the purpose of describing particular embodiments only and is not intended to be limiting of example embodiments of the invention. As used herein, the singular forms "a," "an," and "the," are intended to include the plural forms as well, unless the context clearly indicates otherwise. As used herein, the terms "and/or" and "at least one of" include any and all combinations of one or more of the associated listed items. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof. As used herein, the term "and/or" includes any and all combinations of one or more of the associated listed items. Expressions such as "at least one of," when preceding a list of elements, modify the entire list of elements and do not modify the individual elements of the list. Also, the term "exemplary" is intended to refer to an example or illustration.

When an element is referred to as being "on," "connected to," "coupled to," or "adjacent to," another element, the element may be directly on, connected to, coupled to, or adjacent to, the other element, or one or more other intervening elements may be present. In contrast, when an element is referred to as being "directly on," "directly connected to," "directly coupled to," or "immediately adjacent to," another element there are no intervening elements present.

It should also be noted that in some alternative implementations, the functions/acts noted may occur out of the order noted in the figures. For example, two figures shown in succession may in fact be executed substantially concurrently or may sometimes be executed in the reverse order, depending upon the functionality/acts involved.

Unless otherwise defined, all terms (including technical and scientific terms) used herein have the same meaning as commonly understood by one of ordinary skill in the art to which example embodiments belong. It will be further understood that terms, e.g., those defined in commonly used dictionaries, should be interpreted as having a meaning that is consistent with their meaning in the context of the relevant art and will not be interpreted in an idealized or overly formal sense unless expressly so defined herein.

Before discussing example embodiments in more detail, it is noted that some example embodiments may be described with reference to acts and symbolic representations of operations (e.g., in the form of flow charts, flow diagrams, data flow diagrams, structure diagrams, block diagrams, etc.) that may be implemented in conjunction with units and/or devices discussed in more detail below. Although discussed in a particularly manner, a function or operation specified in a specific block may be performed differently from the flow specified in a flowchart, flow diagram, etc. For example, functions or operations illustrated as being performed serially in two consecutive blocks may actually be performed simultaneously, or in some cases be performed in reverse order. Although the flowcharts describe the operations as sequential processes, many of the operations may be performed in parallel, concurrently or simultaneously. In addition, the order of operations may be re-arranged. The processes may be terminated when their operations are completed, but may also have additional steps not included in the figure. The processes may correspond to methods, functions, procedures, subroutines, subprograms, etc.

Specific structural and functional details disclosed herein are merely representative for purposes of describing example embodiments of the present invention. This invention may, however, be embodied in many alternate forms and should not be construed as limited to only the embodiments set forth herein.

Units and/or devices according to one or more example embodiments may be implemented using hardware, software, and/or a combination thereof. For example, hardware devices may be implemented using processing circuitry such as, but not limited to, a processor, Central Processing Unit (CPU), a controller, an arithmetic logic unit (ALU), a digital signal processor, a microcomputer, a field programmable gate array (FPGA), a System-on-Chip (SoC), a programmable logic unit, a microprocessor, or any other device capable of responding to and executing instructions in a defined manner. Portions of the example embodiments and corresponding detailed description may be presented in terms of software, or algorithms and symbolic representations of operation on data bits within a computer memory. These descriptions and representations are the ones by which those of ordinary skill in the art effectively convey the substance of their work to others of ordinary skill in the art. An algorithm, as the term is used here, and as it is used generally, is conceived to be a self-consistent sequence of steps leading to a desired result. The steps are those requiring physical manipulations of physical quantities. Usually, though not necessarily, these quantities take the form of optical, electrical, or magnetic signals capable of being stored, transferred, combined, compared, and otherwise manipulated. It has proven convenient at times, principally for reasons of common usage, to refer to these signals as bits, values, elements, symbols, characters, terms, numbers, or the like.

It should be borne in mind, however, that all of these and similar terms are to be associated with the appropriate physical quantities and are merely convenient labels applied to these quantities. Unless specifically stated otherwise, or as is apparent from the discussion, terms such as "processing" or "computing" or "calculating" or "determining" of "displaying" or the like, refer to the action and processes of a computer system, or similar electronic computing device/hardware, that manipulates and transforms data represented as physical, electronic quantities within the computer system's registers and memories into other data similarly represented as physical quantities within the computer system memories or registers or other such information storage, transmission or display devices.

In this application, including the definitions below, the term 'module' or the term 'controller' may be replaced with the term 'circuit.' The term 'module' may refer to, be part of, or include processor hardware (shared, dedicated, or group) that executes code and memory hardware (shared, dedicated, or group) that stores code executed by the processor hardware.

The module may include one or more interface circuits. In some examples, the interface circuits may include wired or wireless interfaces that are connected to a local area network (LAN), the Internet, a wide area network (WAN), or combinations thereof. The functionality of any given module of the present disclosure may be distributed among multiple modules that are connected via interface circuits. For example, multiple modules may allow load balancing. In a further example, a server (also known as remote, or cloud) module may accomplish some functionality on behalf of a client module.

Software may include a computer program, program code, instructions, or some combination thereof, for independently or collectively instructing or configuring a hardware device to operate as desired. The computer program and/or program code may include program or computer-readable instructions, software components, software modules, data files, data structures, and/or the like, capable of being implemented by one or more hardware devices, such as one or more of the hardware devices mentioned above. Examples of program code include both machine code produced by a compiler and higher level program code that is executed using an interpreter.

For example, when a hardware device is a computer processing device (e.g., a processor, Central Processing Unit (CPU), a controller, an arithmetic logic unit (ALU), a digital signal processor, a microcomputer, a microprocessor, etc.), the computer processing device may be configured to carry out program code by performing arithmetical, logical, and input/output operations, according to the program code. Once the program code is loaded into a computer processing device, the computer processing device may be programmed to perform the program code, thereby transforming the computer processing device into a special purpose computer processing device. In a more specific example, when the program code is loaded into a processor, the processor becomes programmed to perform the program code and operations corresponding thereto, thereby transforming the processor into a special purpose processor.

Software and/or data may be embodied permanently or temporarily in any type of machine, component, physical or virtual equipment, or computer storage medium or device, capable of providing instructions or data to, or being interpreted by, a hardware device. The software also may be distributed over network coupled computer systems so that the software is stored and executed in a distributed fashion. In particular, for example, software and data may be stored by one or more computer readable recording mediums, including the tangible or non-transitory computer-readable storage media discussed herein.

Even further, any of the disclosed methods may be embodied in the form of a program or software. The program or software may be stored on a non-transitory computer readable medium and is adapted to perform any one of the aforementioned methods when run on a computer device (a device including a processor). Thus, the non-transitory, tangible computer readable medium, is adapted to store information and is adapted to interact with a data processing facility or computer device to execute the program of any of the above mentioned embodiments and/or to perform the method of any of the above mentioned embodiments.

Example embodiments may be described with reference to acts and symbolic representations of operations (e.g., in the form of flow charts, flow diagrams, data flow diagrams, structure diagrams, block diagrams, etc.) that may be implemented in conjunction with units and/or devices discussed in more detail below. Although discussed in a particularly manner, a function or operation specified in a specific block may be performed differently from the flow specified in a flowchart, flow diagram, etc. For example, functions or operations illustrated as being performed serially in two consecutive blocks may actually be performed simultaneously, or in some cases be performed in reverse order.

According to one or more example embodiments, computer processing devices may be described as including various functional units that perform various operations and/or functions to increase the clarity of the description. However, computer processing devices are not intended to be limited to these functional units. For example, in one or more example embodiments, the various operations and/or functions of the functional units may be performed by other ones of the functional units. Further, the computer processing devices may perform the operations and/or functions of the various functional units without sub-dividing the operations and/or functions of the computer processing units into these various functional units.

Units and/or devices according to one or more example embodiments may also include one or more storage devices. The one or more storage devices may be tangible or non-transitory computer-readable storage media, such as random access memory (RAM), read only memory (ROM), a permanent mass storage device (such as a disk drive), solid state (e.g., NAND flash) device, and/or any other like data storage mechanism capable of storing and recording data. The one or more storage devices may be configured to store computer programs, program code, instructions, or some combination thereof, for one or more operating systems and/or for implementing the example embodiments described herein. The computer programs, program code, instructions, or some combination thereof, may also be loaded from a separate computer readable storage medium into the one or more storage devices and/or one or more computer processing devices using a drive mechanism. Such separate computer readable storage medium may include a Universal Serial Bus (USB) flash drive, a memory stick, a Blu-ray/DVD/CD-ROM drive, a memory card, and/or other like computer readable storage media. The computer programs, program code, instructions, or some combination thereof, may be loaded into the one or more storage devices and/or the one or more computer processing devices from a remote data storage device via a network interface, rather than via a local computer readable storage medium. Additionally, the computer programs, program code, instructions, or some combination thereof, may be loaded into the one or more storage devices and/or the one or more processors from a remote computing system that is configured to transfer and/or distribute the computer programs, program code, instructions, or some combination thereof, over a network. The remote computing system may transfer and/or distribute the computer programs, program code, instructions, or some combination thereof, via a wired interface, an air interface, and/or any other like medium.

The one or more hardware devices, the one or more storage devices, and/or the computer programs, program code, instructions, or some combination thereof, may be specially designed and constructed for the purposes of the example embodiments, or they may be known devices that are altered and/or modified for the purposes of example embodiments.

A hardware device, such as a computer processing device, may run an operating system (OS) and one or more software applications that run on the OS. The computer processing device also may access, store, manipulate, process, and create data in response to execution of the software. For simplicity, one or more example embodiments may be exemplified as a computer processing device or processor; however, one skilled in the art will appreciate that a hardware device may include multiple processing elements or processors and multiple types of processing elements or processors. For example, a hardware device may include multiple processors or a processor and a controller. In addition, other processing configurations are possible, such as parallel processors.

The computer programs include processor-executable instructions that are stored on at least one non-transitory computer-readable medium (memory). The computer programs may also include or rely on stored data. The computer programs may encompass a basic input/output system (BIOS) that interacts with hardware of the special purpose computer, device drivers that interact with particular devices of the special purpose computer, one or more operating systems, user applications, background services, background applications, etc. As such, the one or more processors may be configured to execute the processor executable instructions.

The computer programs may include: (i) descriptive text to be parsed, such as HTML (hypertext markup language) or XML (extensible markup language), (ii) assembly code, (iii) object code generated from source code by a compiler, (iv) source code for execution by an interpreter, (v) source code for compilation and execution by a just-in-time compiler, etc. As examples only, source code may be written using syntax from languages including C, C++, C#, Objective-C, Haskell, Go, SQL, R, Lisp, Java®, Fortran, Perl, Pascal, Curl, OCaml, Javascript®, HTML5, Ada, ASP (active server pages), PHP, Scala, Eiffel, Smalltalk, Erlang, Ruby, Flash®, Visual Basic®, Lua, and Python®.

Further, at least one embodiment of the invention relates to the non-transitory computer-readable storage medium including electronically readable control information (processor executable instructions) stored thereon, configured in such that when the storage medium is used in a controller of a device, at least one embodiment of the method may be carried out.

The computer readable medium or storage medium may be a built-in medium installed inside a computer device main body or a removable medium arranged so that it can be separated from the computer device main body. The term computer-readable medium, as used herein, does not encompass transitory electrical or electromagnetic signals propagating through a medium (such as on a carrier wave); the term computer-readable medium is therefore considered tangible and non-transitory. Non-limiting examples of the non-transitory computer-readable medium include, but are not limited to, rewriteable non-volatile memory devices (including, for example flash memory devices, erasable programmable read-only memory devices, or a mask read-only memory devices); volatile memory devices (including, for example static random access memory devices or a dynamic random access memory devices); magnetic storage media (including, for example an analog or digital magnetic tape or a hard disk drive); and optical storage media (including, for example a CD, a DVD, or a Blu-ray Disc). Examples of the media with a built-in rewriteable non-volatile memory, include but are not limited to memory cards; and media with a built-in ROM, including but not limited to ROM cassettes; etc. Furthermore, various information regarding stored images, for example, property information, may be stored in any other form, or it may be provided in other ways.

The term code, as used above, may include software, firmware, and/or microcode, and may refer to programs, routines, functions, classes, data structures, and/or objects. Shared processor hardware encompasses a single microprocessor that executes some or all code from multiple modules. Group processor hardware encompasses a microprocessor that, in combination with additional microprocessors, executes some or all code from one or more modules. References to multiple microprocessors encompass multiple microprocessors on discrete dies, multiple microprocessors on a single die, multiple cores of a single microprocessor, multiple threads of a single microprocessor, or a combination of the above.

Shared memory hardware encompasses a single memory device that stores some or all code from multiple modules. Group memory hardware encompasses a memory device that, in combination with other memory devices, stores some or all code from one or more modules.

The term memory hardware is a subset of the term computer-readable medium. The term computer-readable medium, as used herein, does not encompass transitory electrical or electromagnetic signals propagating through a medium (such as on a carrier wave); the term computer-readable medium is therefore considered tangible and non-transitory. Non-limiting examples of the non-transitory computer-readable medium include, but are not limited to, rewriteable non-volatile memory devices (including, for example flash memory devices, erasable programmable read-only memory devices, or a mask read-only memory devices); volatile memory devices (including, for example static random access memory devices or a dynamic random access memory devices); magnetic storage media (including, for example an analog or digital magnetic tape or a hard disk drive); and optical storage media (including, for example a CD, a DVD, or a Blu-ray Disc). Examples of the media with a built-in rewriteable non-volatile memory, include but are not limited to memory cards; and media with a built-in ROM, including but not limited to ROM cassettes; etc. Furthermore, various information regarding stored images, for example, property information, may be stored in any other form, or it may be provided in other ways.

The apparatuses and methods described in this application may be partially or fully implemented by a special purpose computer created by configuring a general purpose computer to execute one or more particular functions embodied in computer programs. The functional blocks and flowchart elements described above serve as software specifications, which can be translated into the computer programs by the routine work of a skilled technician or programmer.

Although described with reference to specific examples and drawings, modifications, additions and substitutions of example embodiments may be variously made according to the description by those of ordinary skill in the art. For example, the described techniques may be performed in an order different with that of the methods described, and/or components such as the described system, architecture, devices, circuit, and the like, may be connected or combined to be different from the above-described methods, or results may be appropriately achieved by other components or equivalents.

According to a first embodiment, a method is disclosed for segmenting different types of breast structures, including pathologic structures, like cancerous lesions and calcifications and regular structures, like vessels, glandular structures, the nipple, the pectoralis muscle and skin, that are relevant for cancer diagnosis in a DBT volume. In at least one embodiment the method comprises:

Localizing a set of structures in the DBT volume by using at least one multi-stream deep image-to-image network, taking as input at least one image channel; and Segmenting the localized structures by calculating a probability for belonging to a specific type of structure for each voxel in the DBT volume by using at least one multi-stream deep image-to-image network, taking as input at least one image channel for providing a three-dimensional probabilistic map.

In the following the terms used within this application are defined in more detail.

The segmentation does not only refer to cancerous structures, like lesions. It is a major advantage of at least one embodiment of the present invention that not only potential pathologic structures like lesions and calcifications are detected, but also regular (healthy) structures like vessels, skin, muscle and nipple. This has the advantage that navigation and orientation and image processing may be improved.

The method of at least one embodiment has as input a three-dimensional digital breast tomosynthesis (DBT) volume. The output is an augmented image including a three-dimensional probabilistic map, encoding for each voxel the probability of belonging to anatomical structures that are relevant for cancer diagnosis (as mentioned above healthy and pathological structures may be both relevant). The output may be integrated into the original DBT volume or may serve to create a new two- or three-dimension view of the original DBT volume, summarizing the most relevant structures (for example, by enhancing the contours or by highlighting the content etc.).

Localizing and segmenting both refer to a multi-step pipeline. The pipeline may be implemented in software on a computer by using at least one multi-stream deep image-to-image network. Localizing and segmenting may be implemented in hardware structures, in a localizer and in a segmentation unit.

The network is a deep learning (also known as deep structured learning or hierarchical learning) artificial neural network (ANN). It may contain more than one hidden layer. The network uses machine learning methods based on learning data representations, as opposed to task specific algorithms.

Preferably, the learning is supervised or partially supervised. The network may also be composed of one or more convolutional layers. In particular, it may consist of a fully convolutional network that is trained in an end to end fashion with optionally skip connections. It uses pooling and deconvolutional layers. The network takes as input an image/DBT volume and provides as output one or multiple images/volumes.

The network is trained in an end-to-end fashion, e.g. by comparing directly the whole produced output with the whole ground truth, e.g. the whole segmentation mask (instead of considering patches and labels). It might be trained using deep supervision where the loss function includes a combination of costs computed at each level of resolution.

The probabilistic map may include datasets referring to different types of structures (lesion, calcification, anatomical structures etc.). The map includes for each voxel a probability measure for belonging to one of these different structures. For example, for a voxel the following output may be provided and displayed in coded form (highlighted differently in the respective image): 80% tumor tissue, 15% dense tissue and 5% fatty tissue.

In an example embodiment, the method further comprises the following step prior to the step of localizing:

Pre-Classifying the DBT volume in order to provide a pre-classification result, which distinguishes between dense and fatty breast.

The subsequent step of localizing is based on the pre-classification result and is executed specifically with a specific model for dense and with a specific model for fatty breast. Accordingly, the subsequent step of localizing is based on the pre-classification result and is executed specifically with a specific model for dense and with a specific model for fatty tissue. This has the technical advantage that the image processing may be executed much more specifically, considering the differences for dense and fatty breast.

In an example embodiment of the present invention, the step of localizing is based on a five-step procedure, comprising:

Extracting regions of interest;
Generating bounding boxes;
Adjusting the generated bounding box;
Rejecting false positive structures;
Pre-classifying different regions of interest in the DBT volume by providing a class probability to belong to a specific type of structure, including, round mass, spiculated or benign lesions by using a deep convolutional neural network. In this step another kind of network (not a multi-stream deep image-to-image network) is used, because the output is a label (not an image, volume or channel).

In an example embodiment, the step of localizing additionally includes a pre-segmentation as a first step (which is similar to the segmentation, which will be explained below).

In another example embodiment of the present invention, the step of localizing is executed by using an image-to-image multi-scale multi-streams deep learning network, taking as input at least one image channel to generate inverse distance maps to a center of each structure of interest, such as a lesion. The inverse distance maps may be Euclidean and/or geodesic and/or may be computed according to a center of each structure of interest, such as a lesion. The inverse distance maps may also be signed distance maps according to a boundary of the structure of interest.

In another example embodiment of the present invention, for training the network a Tversky loss function (which is a more generic form of the DICE loss function) may be used, that permits to weight the compromise between false positives and false negatives.

In another example embodiment of the present invention, the DBT volume is forwarded as input to multiple—and at least three different—resolution-specific streams and as an output of each of the resolution-specific streams a set of deconvolution layers is followed by activation layers and wherein different outputs of the resolution-specific streams are concatenated using a concatenation layer. By processing the DBT volume at different resolution, this permits to detect and segment structures at different scales. This is very important as lesions for instance show high variation in size.

In another example embodiment of the present invention, the step of localizing is based on generating a bounding box or an ellipsoid for the set of 3D structures (for example ROIs, referring to a possible structure of interest or lesion).

In another example embodiment of the present invention, the step of segmenting is based on procedure, comprising:
Pre-segmenting different types of structures, represented in the DBT volume, including regular structures like skin, vessels, ducts and suspicious structures by way of advanced image processing approaches, including filters, like for example Laplacian or Gaussian or Hessian-based filers, and multi-stream deep image-to-image network;
Structure-specific segmentation by generating for each lesion bounding box candidate a structure-specific prediction channel, encoding the probability for each voxel to belong to a specific type of structure, including a regular or a suspicious structure;
Structure-specific refinement of the structure-specific prediction channels by modeling neighborhood dependencies.
Preferably, the step of refining the calculated probabilities is executed by using Markov random fields or conditional random fields. This can be also done by retrieving similar region/structure of interests plus corresponding masks from a database and aggregating their masks.
Aggregating the calculated different structure-specific prediction channels by fusing the different channels and probabilities and class probabilities by applying:

$$Pred = \Sigma_{c \in classes} P(c) \cdot Pred_c.$$

In another example embodiment of the present invention, the step of segmenting further comprises:
Calculating a class probability by classifying the candidate structure into a specific structure class by using a multi-stream deep image-to-image network.
In another example embodiment of the present invention, the method further comprises the step of:
providing result data for each voxel of the DBT volume, encoding the probability of belonging to a specific type of structure for breast cancer diagnosis. In another embodiment, the result data may further comprise other parameters, like a volume of the structure or lesion, the shape of the structure and/or its distance to nipple and pectoralis. The result data may be overlaid onto the original DBT volume. The result may also be used for creating a new 2D or 3D view of the original DBT volume summarizing and/or enhancing the most relevant information.
In another embodiment, the present invention refers to a computer program loadable into a memory of a digital computer comprising software code portions for executing the method according to one embodiment of the method above, when the computer program is run on the computer. The computer program may also be executed on a plurality of network nodes as a distributed system. The computer program may be stored on a computer readable medium and/or may be downloaded form a server.
According to at least one example embodiment, the invention is directed to an apparatus for segmenting different types of structures, including cancerous lesions and regular structures like vessels and skin, in a DBT volume, comprising:
A localizer for localizing a set of structures in the DBT volume by using a multi-stream deep convolutional neural network;
A segmentation unit for segmenting the localized structures by calculating a probability for belonging to a specific type of structure for each voxel in the DBT volume by using a deep convolutional neural network for providing a three-dimensional probabilistic map.
According to an example embodiment, the apparatus further comprises:
A pre-classification unit which is adapted for providing a pre-classification result by differentiating in the DBT volume between dense and fatty breast,
wherein the pre-classification result is forwarded to the localizer and to the segmentation unit for specific processing of dense and fatty breast.

An embodiment of the present invention refers to a novel processing pipeline based on deep learning for the generation of 3D maps that encodes for each voxel the probability of belonging to a relevant anatomical structure for breast cancer diagnosis given a DBT volume.

The term "structure" may in one embodiment refer to lesions or potential lesions, like tumors, calcifications and others. According to another embodiment, a structure may refer to regular tissue in the breast, like vessels, skin, milk ducts and the nipple. For radiologists it is very helpful to provide such tissue structures in the image, which may be used as a kind of orientation or navigation in the image data. For example, the nipple serves as an important landmark or marker in the image for measuring distances.

Figure 1:
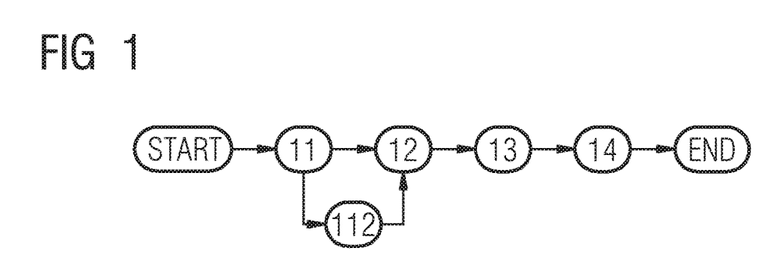
FIG. 1 shows a schematic view of a method for DBT image segmentation based on an example embodiment of the present invention.

FIG. 1 shows a novel processing pipeline, which includes three parts (which may be represented as three method steps):
1) an (optional) pre-classification stage 112,
2) a localization stage 12 for executing the step of localizing and
3) a segmentation stage 13 for executing the step of segmenting.

In a first step 11 the DBT volume is detected or read in and in the last step 14 the result data with a probability map is provided and may be displayed on a screen.

In the first stage, the incoming DBT volume is pre-segmented and pre-classified into fatty or dense breast to enable further class-specific processing/modeling. In the second stage, lesion candidates are localized, i.e. the parameters of their corresponding bounding boxes are inferred. Finally, and in the third stage, probabilities for belonging to relevant anatomical structures for diagnosis, e.g. lesions, ducts, vessels are inferred for each voxel within the volume. The result is a set of 3D probabilistic maps that can be overlaid onto the original DBT volume, used to provide regions of interests or additional information to the radiologist, and integrated as semantic information for further processing such as improved visualization, automatic reporting or decision support.

As depicted in FIG. 1 and explained above, it is preferred to include a pre-classification procedure. This has the technical effect of distinguishing between dense vs fatty breast. However, this procedure is optional. In this stage, the goal is to determine whether the current case shows characteristics of a fatty breast or consists mostly of dense tissues. Within fatty breasts, there are almost no dense structures, so that if lesions are present, they are clearly visible within the image, as they will appear as high density structures. In the case of dense breast, as the major part of the tissues show high density, finding lesions becomes very challenging, even for experienced observers. For this reason, we propose as a very first step to distinguish between dense and fatty cases, so that models (for localization and for segmentation) specific to dense or fatty cases can be applied for subsequent analysis. For deciding whether a case belongs to the fatty or dense breast class, we propose an approach described in FIG. 2.

Figure 2:
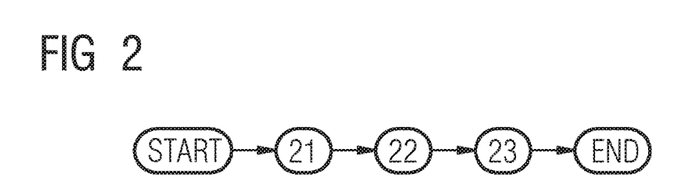
FIG. 2 shows a schematic view of a method for pre-classification of a DBT image in dense versus fatty tissue based on an example embodiment of the present invention.

As shown in FIG. 2, in the first step 21 the DBT volume is detected or read in. In step 22 the read-in data is pre-segmented and in step 23 the image data (voxel wise) are classified in dense and fatty tissue. The goal is to generate from the given DBT volume tissue channels that encode the probability of belonging to following structures:
1) skin,
2) low density tissues,
3) high density tissues,
4) high density and salient tissues and
5) vessel-like tissues.

This pre-segmentation 22 is generated using following processing pipeline.

Extraction of breast mask: this is performed using thresholding to separate tissues from air and keeping the largest connected component.

Extraction of skin line: this is done by computing the Euclidean distance to the mask boundary, a first skin region can be extracted using a pre-defined threshold. This is then refined by keeping only high curvatures regions within this region, curvature being defined as negatives value within Laplacian of Gaussian responses.

Extraction of low density tissues: this is done by using thresholding (that can be learned from data) within breast mask. Voxels below this threshold are labeled as low density.

Extraction of high density tissues: this is done by using the same threshold than in the previous step. Voxels above this threshold are labeled as high density.

Extraction of high density and salient tissues: this is done by using thresholding on Laplacian of Gaussian response or any other type of blob filters. All voxels that belong to high density tissues and that have a negative response on the Laplacian of Gaussian output are labeled as high density and salient.

Extraction of vessel-like tissues: this is done by using filtering approaches that enhances linear structures based on the Hessian matrix and its eigenvectors, such as determinant of hessians.

As depicted in FIG. 2, the next step in the pre-classification pipeline refers to the step of classification 23. The goal of this step is to classify the current case as fatty or dense breast, using the original or raw DBT volume as well as the 5 channels, generated at the previous step. To this end, a fully convolutional deep network (FCN) is trained taking either as input 5 channels, i.e. raw intensities and the 5 tissue channels, or 5 channels, i.e. the element-wise product of the raw intensity with the tissue channels. The FCN includes several convolutional blocks of 4 layers (convolutional+ leaky rectifiers+batchnorm+spatial dropout) followed by pooling layers. At the very end, a stack of convolutional layers with 1×1×1 kernels are used as equivalent for fully connected layers. To model the classification task, the last layer can be a sigmoid activation layer with one single neuron where values towards 0 would encode fatty breast and values towards 1 dense breast, or a softmax layer with two neurons corresponding to each class.

Depending on the (binary: fatty versus dense) output of this step, the current DBT volume will be subsequently processed by models trained specifically for fatty or dense breast. This has the technical effect that the localization procedure 12 and segmentation procedure 13 may be improved significantly due to dedicated specification and determined procedure.

Figure 3:
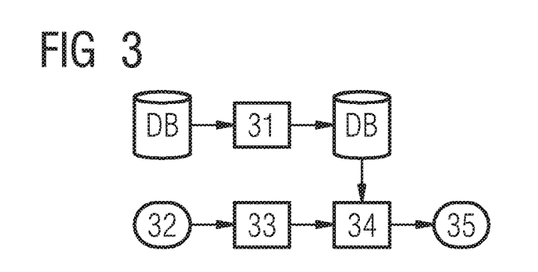
FIG. 3 refers to a schematic representation of a system of an example embodiment, for training a fully convolutional network using data augmentation.

The training procedure for this network is shown on FIG. 3. The database DB serves to store the DBT volume and the corresponding labels (fatty-dense), as processed in the previous step. Data augmentation 31 can be performed to increase the amount of training samples by using simple transformations such as rotation, flipping or intensity changes. This permits to prevent from overfitting in addition to regularization and dropout layers. The training and cross validation set may, then, be stored in the database DB, too. Architecture parameters 32 are fed into the FCN for network initialization 33. Supervised learning is depicted in FIG. 3 with reference numeral 34. A trained classifier 35 may be provided. The cost function used can be in this case binary cross entropy and the optimizer for instance an Adam optimizer.

After having pre-classified the DBT volume, the next step in the processing pipeline, shown in FIG. 1, is the step of localizing 12.

The goal of this localization stage (step of localizing 12) is to detect a set of lesion candidates, i.e. to infer the 6 parameters of their bounding boxes (position x,y,z and scale sx,sy,sz). As shown FIG. 4 and FIG. 6, two possible embodiments are proposed.

Figure 4:
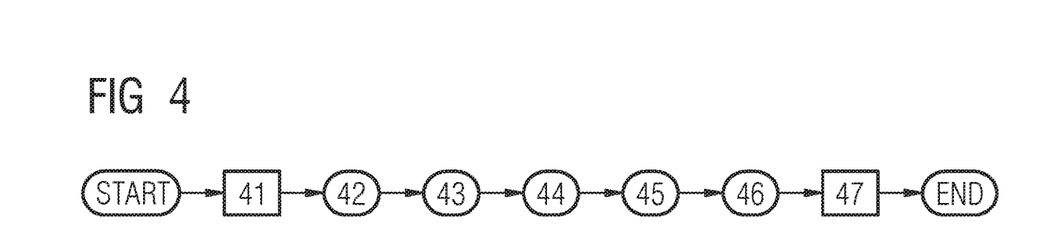
FIG. 4 shows an example embodiment of a localizing pipeline with 5 steps.

The first embodiment of localizing 12 is presented in FIG. 4 and includes 5 core steps:
1) regions of interest extraction, 42
2) bounding box generation, 43
3) bounding box adjustments, 44
4) false positive rejection 45 and
5) pre-classification 46.

In the first step 41 the DBT volume is detected or read in and in the last step 47 the result, including a probability map is visualized on a display unit on demand for each voxel.

Figure 5:
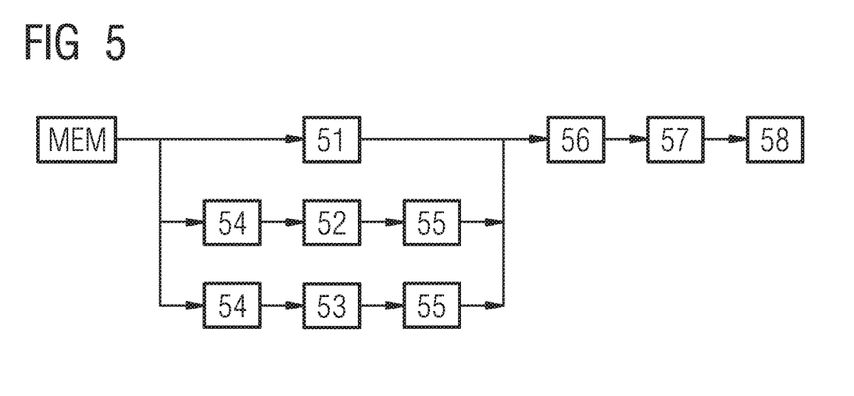
FIG. 5 shows a multi-streams multi-scale region of interest extraction according to an example embodiment of the present invention.

The first embodiment of a localization processing pipeline is explained in more detail below, with respect to FIG. 4.
Regions of Interest Extraction 42:

Given the raw DBT volume, this first step aims at generating a probability map that encodes the probability of belonging to a region of interest (ROI) represented either as a bounding box or as an ellipsoid. To this end, a multi-stream deep convolutional network such as the one detailed in FIG. 5 is trained end to end relating directly the raw image to a mask encoding voxel-wise the lesion bounding boxes or ellipsoid regions. In this example, the input is forwarded to three different streams:
  i) full resolution subnet,
  ii) intermediate resolution subnet and
  iii) the coarse resolution subnet.

FIG. 5 shows a multi-streams multi-scale ROI extraction system with a storage unit MEM for providing the raw DBT volume. In this example three different streams are used: full resolution subnet 51, an intermediate resolution subnet 52 and a coarse resolution subnet 53. It has to be noted that more than three streams could be used if needed.

Figure 9:
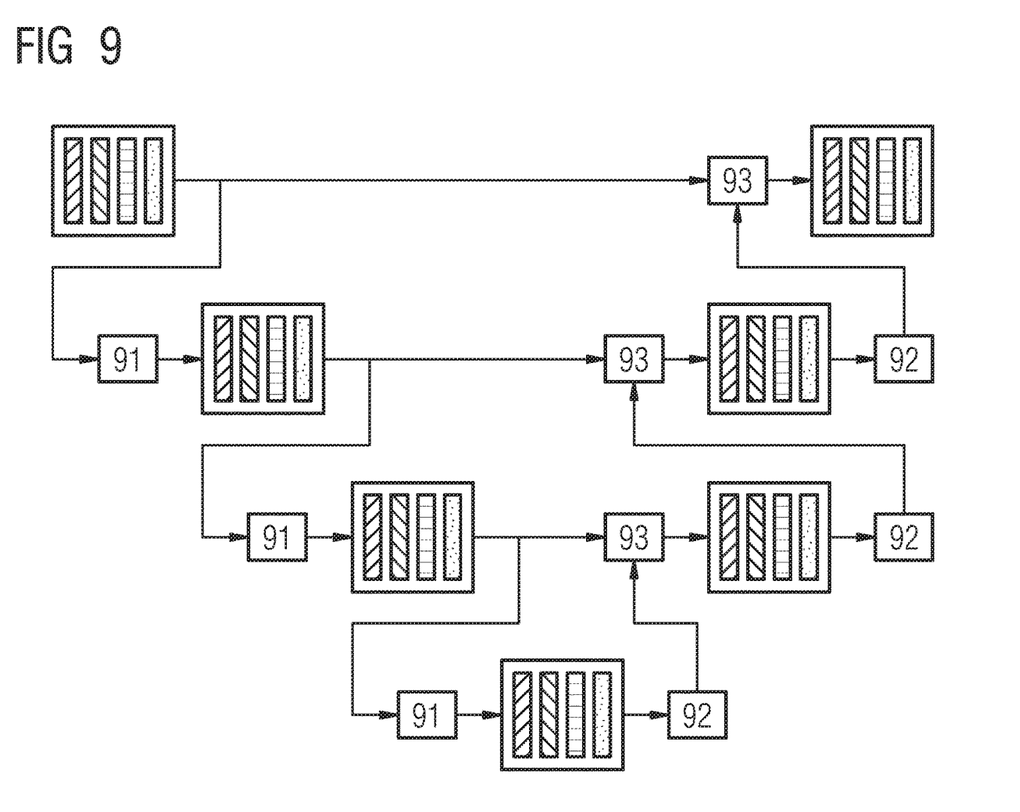
FIG. 9 refers to a schematic representation of a scale specific subnet including convolutional blocks, pooling, skip connections, deconvolutions and concatenation layers.

For each resolution specific stream, a pooling layer 54 is used for generating lower resolution version of the input using either max or average pooling operations. Then at the output of each stream, a deconvolution layer followed by an activation layer such as rectified linear unit (ReLU) 55 is used for upsampling the prediction to the original resolution. The reference numeral 55 refers to both units (deconvolution and ReLU). The different outputs are then concatenated using a concatenation layer 56 and forwarded to a stack of 1×1×1 convolution layers 57 as equivalent for fully connected layers. The output layer 58 modeling the classification task can be a sigmoid or a softmax layer. A subnet example is shown in FIG. 9.
Bounding Box Generation 43:

Thresholding and connected components analysis applied to the map resulting from previous step to extract bounding box candidates. Non-local maxima suppression can be further performed especially in the case where candidates appearing at several scales are present.

Bounding Box Adjustments 44:

Using a deep convolutional neural network, adjust the position of the bounding boxes obtained at the previous step in order to maximize the overlap ratio with the target bounding boxes. This can be done using a similar network as mentioned before with respect to the pre-classification step, but trained in a regression fashion, i.e. trained to predict the offset between the candidate bounding box and the target box. During training, sum of square differences or jaccard loss can be used. Moreover, we propose to regress a quality measure such as the intersection over union to infer the confidence of the network about its prediction. This measure is then used to rank the candidates to keep only the best subset, and as additional input for the next step dealing with false positive detection.

False Positive Rejection 45:

The goal of this step is to further reduce the number of candidates to remove possible false positive. We propose to use here a well a deep convolutional network as described by FIG. 3. Note that to train this network, one needs to mine so called hard negatives, which are difficult to distinguish from lesion ROIs. In addition to the raw DBT volume, this network takes the predicted intersection over union from the previous step. This estimate can be concatenated at a deeper level within the network.

Pre-Classification 46:

Given the raw DBT volume, the goal of this step is to provide for each remaining bounding box candidate the probability to belong to a round mass, spiculated or benign lesion. This is also done by using a deep convolutional network.

Figure 6:
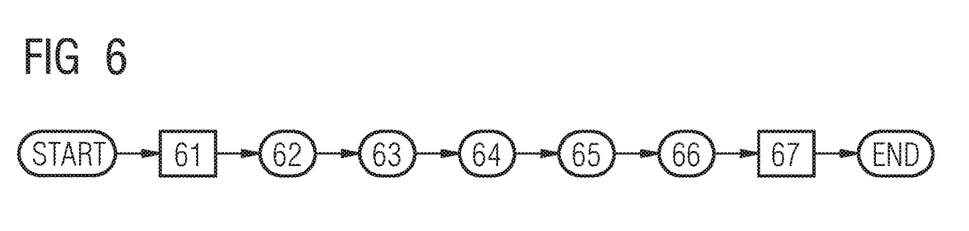
FIG. 6 shows another embodiment of a localizing pipeline with 5 core steps.

The second embodiment is presented in FIG. 6 showing a multi-streams multi-scale ROI extraction and includes 5 core steps:
1) pre-localization of lesion candidates 62,
2) candidates extraction 63,
3) localization 64,
4) false positive rejection 65 and
5) pre-classification 66.

In the first step 61 the DBT volume is detected or read in and in the last step 67 the result, including a probability map is visualized on a display unit on demand for each voxel.

Pre-Localization 62:

In this embodiment, it is proposed to use end to end deep learning to generate inverse distance map to lesion centers. As in the previous embodiment, it is proposed to use a multi-scale, i.e. multi-streams network. Note that the inverse distance map can be computed using the Euclidean distance but alternatively it can integrate intensity information by using a Geodesic distance.

Candidates Extraction 63:

Mean shift clustering or thresholding and connected components analysis applied to the map resulting from previous step as an example embodiment. Non-local maxima suppression could be added if several scales are used.

Localization 64:

Similarly, as in the previous embodiment, a deep convolutional neural network is used to predict the offset from center location to the corners of the bounding box, deriving thereby its parameters. As in the previous embodiment, we propose to regress the intersection over union value as quality measure.

False Positive Rejection 65:

This step is similar as in the previous embodiment. A deep convolutional network is used to classify bounding box content as either false positive or not.

Pre-Classification 66:

This step is similar as in the previous embodiment. A deep convolutional network is used to provide for each bounding box its probability to belong to a round mass, speculated or benign lesion and provide the same as intermediate result.

After having finished the localization procedure 12 (shown in FIG. 1), the intermediate result of this procedure is forwarded and used in the next procedure, the segmentation procedure 13, which will be describe below with reference to FIG. 7.

The goal of this segmentation stage (step of segmenting 13) is to generate the different probabilistic channels encoding the probability of belonging to a relevant structure for cancer diagnosis. First, regular structures such as skin, vessels and ducts need to be segmented. Second, using the detected bounding box from the previous stage, the probability of the voxels to belong to a suspicious structure, e.g. cancerous lesion needs to be inferred. As shown on FIG. 7 and FIG. 10, we propose two possible embodiments.

Figure 7:
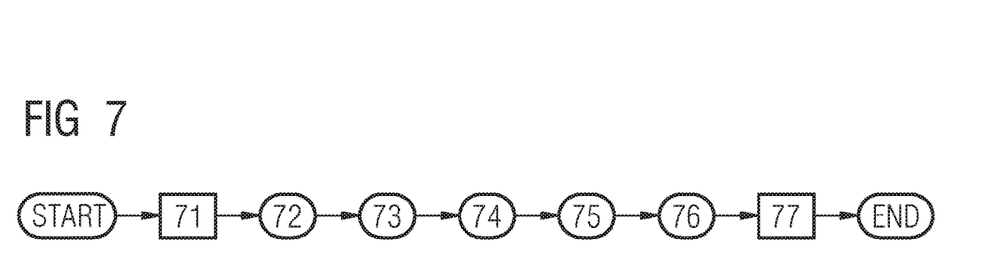
FIG. 7 depicts a segmentation phase with 5 core steps according to an example embodiment of the present invention.

The example embodiment of segmenting 13 is shown in FIG. 7 and includes 5 core steps:
1) pre-segmentation 72,
2) lesion-specific segmentation 73,
3) lesion-specific refinement 74,
4) classification 75 as an optional step and
5) aggregation 76.

In the first step 71 the DBT volume is detected or read in and in the last step 77 the result, including a probability map is visualized on a display unit on demand for each voxel.

Pre-Segmentation 72:

In this stage, the goal is to generate tissue probability maps that encode the probability of belonging to anatomical structures that are relevant for cancer diagnosis, e.g. skin, vessels, and ducts. To this end, we propose a two-steps approach, including a rough pre-segmentation and tissue segmentation. The rough segmentation is performed similarly as in the previous stage, 5 different types of structures channels are generated: 1) skin, 2) low density tissues, 3) high density tissues, 4) high density and salient tissues and 5) vessel-like structures. Providing a first rough voxel-wise encoding, these 5 channels are forwarded to the next step which is tissue segmentation.

In this second step, we propose to use a deep convolutional network trained in an end to end fashion such as the one presented in FIG. 9. It provides multi-class output by using a softmax layer as very last layer. It can be trained by using multi-class cross entropy or some more advanced segmentation losses as well will describe in the next section.

Lesion-Specific Segmentation 73:

Given the raw DBT volume and the tissue channels computed in the previous step, the goal of the lesion-specific segmentation is to generate for each lesion bounding box candidate so-called lesion-specific channels. Each output channel encodes the probability for each voxel to belong to a specific type of lesion, namely round masses, spiculated lesions or benign lesions. Therefore, a dedicated deep convolutional network is trained for each type of lesions. To provide voxel-wise predictions at full resolution, we propose to use a multi-streams end-to-end fully convolutional network as shown on FIG. 8.

Figure 8:
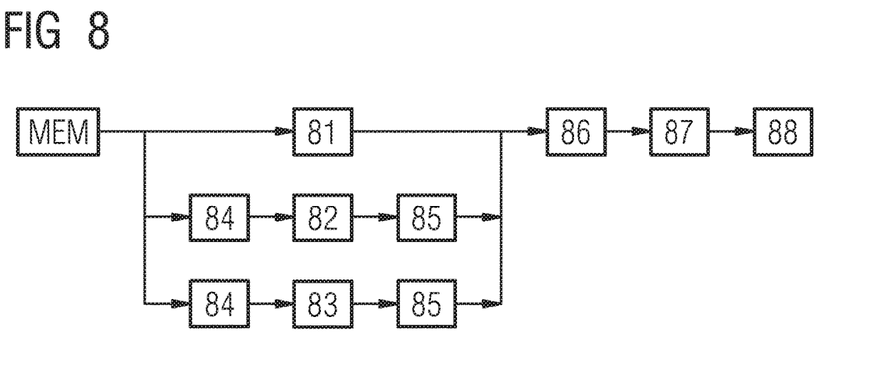
FIG. 8 shows a multi-streams lesion or structure specific end to end fully convolutional network according to an example embodiment of the present invention.

FIG. 8 shows a lesion-specific multi-streams end-to-end fully convolutional network. The memory MEM is adapted to provide or store the raw DBT volume data and the tissue channels.

As already described in the localization stage, all channels are forwarded to three different streams 81, 82, 83:
i) full resolution subnet 81,
ii) intermediate resolution subnet 82 and
iii) the coarse resolution subnet 83.

Note that more than three streams could be used if needed. For each resolution specific stream, a pooling layer 84 is used for generating lower resolution version of the input using either max or average pooling operation. Then at the output of each stream, a deconvolution layer followed by an activation layer such as rectified linear unit (ReLU) 85 is used for upsampling the prediction to the original resolution. The different outputs are then concatenated using a concatenation layer 86 and forwarded to a stack of 1×1×1 convolution layers 87 as equivalent for fully connected layers. The output layer 88 modeling the classification task can be a sigmoid or a softmax layer. A subnet example is shown on FIG. 9.

FIG. 9 shows a scale-specific subnet including convolutional blocks, pooling, skip connections, deconvolution and concatenation layers. A convolutional layer is represented in FIG. 9 with hashed lines from left downwards to right upwards. Leaky Rectifiers are represented in hashed lines from left upwards to right downwards. In FIG. 9 a Batchnorm is represented in horizontally hashed lines and Spatial Dropout is represented in dotted manner. Pooling is represented in FIG. 9 via reference numeral 91, a deconvolution+ rectified linear unit (ReLU) together have reference numeral 92 and the concatenation layer is depicted in FIG. 9 with numeral 93.

In this example, a U-net type of architecture is used where skip connections are used to feed earlier output at higher resolutions at later stage. This has been shown to permit to increase the quality of predictions in terms of resolution, which is crucial for segmentation. Further skip connections can be also used to learn residuals when more convolutional blocks are used. Using DBT volumes, the tissue channels and their associated ground truth segmentation masks, the whole network is trained in an end to end fashion, i.e. for a given tuple ([DBT,TissueChannels],Ground Truth), the output of the network Pred is compared directly to the whole mask GT (GT stands for Ground Truth). While this permits to take into account the context of the whole volume, it requires a careful choice for the cost function to optimize. Indeed, if there is high imbalance between background and class of interest, binary cross entropy might be badly impacted towards the background class. To avoid this issue, we introduce a new loss function based on the Tversky index, which is a more generic version of the DICE coefficient.

$$Tversky(GT, Pred) = 1 - \frac{|Pred \cap GT|}{|Pred \cap GT| + \alpha.|Pred - GT| + (1-\alpha).|GT - Pred|}$$

With an extra parameter a one can control the impact of false positives. If α=0.5, the Tversky index becomes the DICE coefficient. Note that this loss is differentiable, and the intersection and relative complements are computed using element-wise product operations. While this loss is perfect in the case where a lesion, e.g. foreground is present, it does not provide any valuable information for a negative case (as the intersection becomes 0). To be able to learn also from negative cases, we propose to use a weighted multi-class version of this loss:

$$Tversky_{global} = \sum_{c \in classes} \alpha_c.Tversky_c$$

Lesion-Specific Refinement 74:

In this step, refinement of the lesion-specific prediction channels is performed by using approaches that models neighborhood dependencies such as Markov random fields (MRF) or Conditional random fields (CRF). In an example embodiment, CRF is used as their pairwise terms conditioned on the original volume permits usually to achieve better segmentation performance.

Classification 75 (Optional):

Given the original image, e.g. a region of interest defined by a candidate bounding box, and all lesion-specific prediction channels, the goal of this optional step is to classify the current candidate into one of the different lesion class. This is done by using a fully convolutional network similar to the one described above with respect to the step of pre-classification. The output is a probability distribution over the different lesion classes in the form of a class histogram.

Aggregation 76:

Given the different lesion-specific prediction channels and the probability distribution over the different lesion classes provided by the previous step or by the classification step in the localization stage, or both, the final segmentation output is generated by fusing the different channels based on the class probabilities:

$$Pred = \sum_{c \in classes} P(c).Pred_c$$

If class probabilities are available from both localization and segmentation step, these can be averaged to provide the factors P(c). While model averaging permits to achieve better results, using class probabilities to weight their contributions permits to give more weight to the channel coming from the most probable lesion-specific model.

Figure 10:
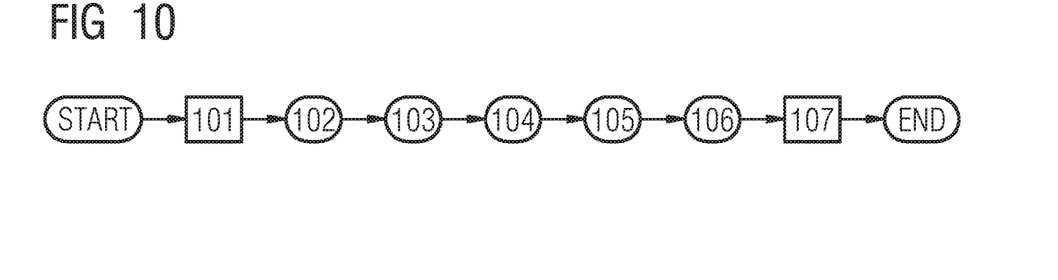
FIG. 10 depicts a segmentation phase with 5 core steps according to another example embodiment of the present invention.

Another example embodiment for the segmentation step 13 is shown in FIG. 10 and includes 5 core steps:
1) pre-segmentation 102,
2) lesion-specific encoding 103,
3) code aggregation 104,
4) retrieval 105 and
5) aggregation 106.

In the first step 101 the DBT volume is detected or read in and in the last step 107 the result, including a probability map is visualized on a display unit on demand for each voxel.

Pre-Segmentation 102:

This step is similar to the one described in the previous section.

Lesion-Specific Encoding 103:

Using raw volumes and the tissue channels provided by the pre-segmentation step, the goal is to generate a compact representation for the considered region of interest. To this end, we propose to use deep convolutional auto-encoder with several convolutional blocks with 4 (four) layers and followed by pooling layers, dropout, sigmoid and a flattening layer. Looking quite similar to a fully convolutional network for classification, it ends with a flattening layer to reshape the output to a vector. This vector is a compact latent representation of the visual context contained within the region of interest. To train such a deep convolutional auto-encoder, one needs to train simultaneously a decoder network which is very similar to the encoder network with the only difference is that its role is to reconstruct the input volume+channels. One can use shared weights between encoding and decoding networks or different weights. Usually, noise is added to the input volume and channels to improve the training of the whole encoding and decoding pipeline. The loss function is based on the reconstruction error computed by comparing the original volume and its reconstruction. We propose to train such a deep convolutional auto-encoder for each type of lesions. As a result, a set of lesion-specific signatures are generated by this step.

Figure 11:
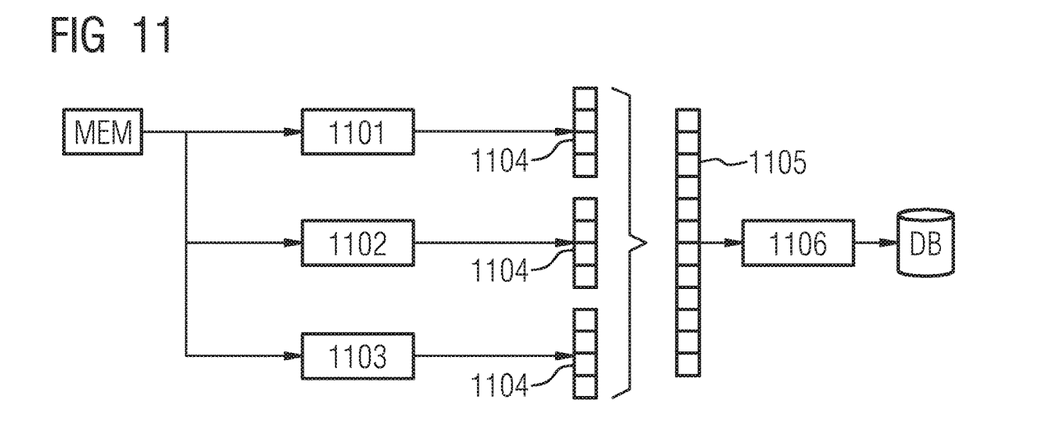
FIG. 11 shows in a schematic manner a system for extraction of compact signatures form candidate regions of interest of most similar regions from a database of ROIs with corresponding segmentations masks according an example embodiment of the present invention and FIG. 12 is a schematic overview figure of a localization and segmentation system according to an example embodiment of the present invention.

Code Aggregation 104:

Given the lesion-specific signatures from the previous step, a global signature is generated for the considered candidate region of interest by concatenating the lesion-specific signatures into one large vector as shown in FIG. 11.

FIG. 11 depicts a system for extraction of compact signatures from candidate region of interest (ROI) and retrieval of most similar regions from a database of ROIs with corresponding segmentation masks. Memory MEM stores the raw DBT volume and four (4) tissue channels. A first lesion-specific encoder 1101, a second lesion-specific encoder 1102 and a third lesion-specific encoder 1103 are used, which serve to provide lesion specific-signatures 1104 and a global signature 1105. In 1106 most similar regions are retrieved. The result may be stored in the database DB by encoding ROIs and corresponding segmentation masks.

Retrieval 105:

Using the compact representation provided by the previous step, a set of N similar regions of interest and their corresponding ground truth segmentation masks are retrieved from a large database. To assess similarity between the candidate region and regions within the database, their global signatures can be compared by using L2, L1 or L0 norm, i.e. Euclidean, Manhattan or Hamming distance.

Aggregation 106:

Finally, a final prediction channel is created by aggregating the segmentation masks retrieved from the database. This can be simply averaged or linearly combined depending on their distance to the query candidate.

$$Pred = \sum_{k \in retrieved\ examples} w_k M_k$$

M being the ground truth mask of a given retrieved example.

Figure 12:
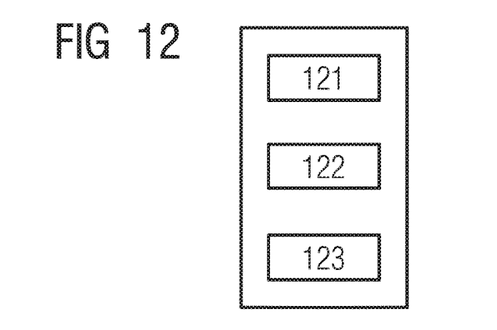

FIG. 12 shows a system for segmentation of anatomical structures according to an example embodiment, comprising at least a localizer 122 and a segmentation unit 123. The localizer 122 is adapted to execute the localizing pipeline 12 and the segmentation unit is adapted to execute the segmentation pipeline 13, mentioned above with respect to FIG. 1. In the example embodiment, shown in FIG. 12, the system additionally comprises a pre-classifier 121, which is adapted to execute the pre-classification 112, mentioned above.

In sum, embodiments of the present invention, refer to a fully automatic pipeline based on deep learning that permits—given a DBT volume—to generate 3D maps encoding for each voxel the probability of belonging to anatomical structures that are relevant for breast cancer diagnosis. The proposed approach embodies a crucial part for supporting radiologists in their increasing workload when working with DBT images. Indeed, as described in the previous section, the resulting 3D probabilistic maps can be overlaid onto the original DBT volume, used to provide regions of interests or additional information to the radiologist, and integrated as semantic information for further processing such as improved visualization, automatic reporting or decision support.

All features discussed or shown with respect to particular embodiments of the invention can be provided in various combinations in order to simultaneously realize their positive technical effects.

All method steps can be implemented by device(s) that are adapted for performing the corresponding method step. All functions that are performed by particular device(s) or apparatus modules can be implemented as a method step of a corresponding method, respectively.

The scope of the present invention is given by the claims and is not restricted by features discussed in the description or shown in the figures.

The patent claims of the application are formulation proposals without prejudice for obtaining more extensive patent protection. The applicant reserves the right to claim even further combinations of features previously disclosed only in the description and/or drawings.

References back that are used in dependent claims indicate the further embodiment of the subject matter of the main claim by way of the features of the respective dependent claim; they should not be understood as dispensing with obtaining independent protection of the subject matter for the combinations of features in the referred-back dependent claims. Furthermore, with regard to interpreting the claims, where a feature is concretized in more specific detail in a subordinate claim, it should be assumed that such a restriction is not present in the respective preceding claims.

Since the subject matter of the dependent claims in relation to the prior art on the priority date may form separate and independent inventions, the applicant reserves the right to make them the subject matter of independent claims or divisional declarations. They may furthermore also contain independent inventions which have a configuration that is independent of the subject matters of the preceding dependent claims.

None of the elements recited in the claims are intended to be a means-plus-function element within the meaning of 35 U.S.C. § 112(f) unless an element is expressly recited using the phrase "means for" or, in the case of a method claim, using the phrases "operation for" or "step for."

Example embodiments being thus described, it will be obvious that the same may be varied in many ways. Such variations are not to be regarded as a departure from the spirit and scope of the present invention, and all such modifications as would be obvious to one skilled in the art are intended to be included within the scope of the following claims.

What is claimed is:

1. A method for segmenting a set of structures, including pathologic breast structures and regular breast structures, in a digital breast tomosynthesis (DBT) volume, comprising:
   pre-classifying the DBT volume to provide a pre-classification result, the pre-classification result distinguishing between dense tissue and fatty tissue;
   localizing a set of structures in the DBT volume by using at least one multi-stream deep image-to-image network, taking as input at least one image channel; and
   segmenting the set of structures by calculating a probability for belonging to a specific type of structure, for each voxel in the DBT volume, by using at least one multi-stream deep image-to-image network, taking as input at least one image channel for providing a three-dimensional probabilistic map, wherein at least one of the localizing is based on the pre-classification result and is executed with a specific model for dense tissue and with a specific model for fatty tissue and the segmenting is based on the pre-classification result and is executed with a specific model for dense tissue and with a specific model for fatty tissue.

2. The method of claim 1, wherein the localizing is executed by using an image-to-image multi-scale multi-streams deep learning network, taking as input at least one image channel to generate inverse distance maps to a center of each structure of interest.

3. The method of claim 2, wherein the inverse distance maps are at least one of Euclidean, geodesic, are computed according to the center of each structure of interest, and are signed distance maps according to a boundary of the structure of interest.

4. The method of claim 1, wherein for training the network, a Tversky loss function is used.

5. The method of claim 4, wherein the Tversky loss function is a DICE loss function.

6. The method of claim 1, wherein the DBT volume is forwarded as input to multiple resolution-specific streams and as an output of each of the resolution-specific streams a set of deconvolution layers is followed by activation layers and wherein different outputs of the resolution-specific streams are concatenated using a concatenation layer.

7. The method of claim 1, wherein the localizing is based on generating a bounding box or an ellipsoid for the set of structures.

8. The method of claim 7, wherein the segmenting is based on procedure, comprising:

pre-segmenting different types of structures, represented in the DBT volume, including regular structures and suspicious structures by way of filters and multi-stream deep image-to-image network;

structure-specific segmenting by generating, for each lesion bounding box, a candidate structure-specific prediction channel, encoding a probability for each voxel to belong to a specific type of structure, including a regular structure or a suspicious structure;

structure-specific refining of the structure-specific prediction channels by modeling neighborhood dependencies; and aggregating the structure-specific prediction channels, once refined, by fusing the structure-specific prediction channels and probabilities and class probabilities by applying:

$$\text{Pred} = \Sigma_{c \in classes} P(c) \cdot \text{Pred}_c.$$

9. The method of claim 8, wherein the segmenting further comprises:

calculating a class probability by classifying the candidate structure into a specific structure class by using a multi-stream deep image-to-image network.

10. The method of claim 1, further comprising:

providing result data for each voxel of the DBT volume, and encoding a probability of belonging to a specific type of structure for breast cancer diagnosis.

11. A memory storing software code portions for executing the method of claim 1, when the software code portions are run on a computer.

12. A non-transitory computer readable medium including program code for carrying out the method of claim 1 when the program code is run on a computer.

13. The method of claim 1, wherein the localizing is based on a procedure, comprising:

extracting regions of interest;
generating bounding boxes;
adjusting the bounding boxes;
rejecting false positive structures; and
pre-classifying different regions of interest in the DBT volume by providing a class probability to belong to a specific type of structure, including, round mass, spiculated or benign lesions by using a deep convolutional neural network.

14. The method of claim 1, wherein the localizing is executed by using an image-to-image multi-scale multi-streams deep learning network, taking as input at least one image channel to generate inverse distance maps to a center of each structure of interest.

15. The method of claim 14, wherein the inverse distance maps are at least one of Euclidean, geodesic, are computed according to the center of each structure of interest, and are signed distance maps according to a boundary of the structure of interest.

16. A method for segmenting a set of structures, including pathologic breast structures and regular breast structures, in a digital breast tomosynthesis (DBT) volume, comprising:

localizing a set of structures in the DBT volume by using at least one multi-stream deep image-to-image network, taking as input at least one image channel; and segmenting the set of structures by calculating a probability for belonging to a specific type of structure, for each voxel in the DBT volume, by using at least one multi-stream deep image-to-image network, taking as input at least one image channel for providing a three-dimensional probabilistic map, wherein the localizing is based on a procedure, comprising:

extracting regions of interest;
generating bounding boxes;
adjusting the bounding boxes;
rejecting false positive structures; and
pre-classifying different regions of interest in the DBT volume by providing a class probability to belong to a specific type of structure, including, round mass, spiculated or benign lesions by using a deep convolutional neural network.

17. A non-transitory computer readable medium including program code for carrying out the method of claim 16 when the program code is run on a computer.

18. A memory storing software code portions for executing the method of claim 16, when the software code portions are run on a computer.

19. An apparatus for segmenting different types of structures, including cancerous lesions and regular structures, in a digital breast tomosynthesis (DBT) volume, comprising:

a localizer to localize a set of structures in the DBT volume by using a multi-stream deep convolutional neural network; and a segmenter to segment the localized set of structures by calculating a probability for belonging to a specific type of structure, for each voxel in the DBT volume, by using a deep convolutional neural network for providing a three-dimensional probabilistic map, wherein localizer is configured to localize the set of structures based on a procedure, comprising:

extracting regions of interest;
generating bounding boxes;

adjusting the bounding boxes;
rejecting false positive structures; and
pre-classifying different regions of interest in the DBT volume by providing a class probability to belong to a specific type of structure, including, round mass, spiculated or benign lesions by using a deep convolutional neural network.

20. The apparatus of claim 19, further comprising:
a pre-classifier, configured to provide a pre-classification result, the pre-classification result differentiating in the DBT volume between dense tissue and fatty tissue, wherein the pre-classification result is forwarded to at least one of the localizer and the segmenter, for specific processing of dense tissue and fatty tissue.

21. The apparatus of claim of claim 20, wherein at least one of
the specific processing includes localizing, by the localizer, is based on the pre-classification result and is executed with a specific model for dense tissue and with a specific model for fatty tissue; and
the specific processing includes segmenting, by the segmenter, is based on the pre-classification result and is executed with a specific model for dense tissue and with a specific model for fatty tissue.

22. An apparatus for segmenting different types of structures, including cancerous lesions and regular structures, in a digital breast tomosynthesis (DBT) volume, comprising:
a pre-classifier to pre-classify the DBT volume to provide a pre-classification result, the pre-classification result distinguishing between dense tissue and fatty tissue;
localizer to localize a set of structures in the DBT volume by using a multi-stream deep convolutional neural network; and
a segmenter to segment the localized set of structures by calculating a probability for belonging to a specific type of structure, for each voxel in the DBT volume, by using a deep convolutional neural network for providing a three-dimensional probabilistic map, wherein at least one of
the localizer is configured to localize the set of structures based on the pre-classification result and is configured to execute with a specific model for dense tissue and with a specific model for fatty tissue and
the segmenter is configured to segment the localized set based on the pre-classification result and is configured to execute with a specific model for dense tissue and with a specific model for fatty tissue.

23. The apparatus of claim 22, wherein the localizer is configured to localize the set of structures based on a procedure, comprising:
extracting regions of interest;
generating bounding boxes;
adjusting the bounding boxes;
rejecting false positive structures; and
pre-classifying different regions of interest in the DBT volume by providing a class probability to belong to a specific type of structure, including, round mass, spiculated or benign lesions by using a deep convolutional neural network.

* * * * *